United States Patent [19]

Arai et al.

[11] Patent Number: 4,837,149
[45] Date of Patent: Jun. 6, 1989

[54] NOVEL SAFRAMYCIN A DERIVATIVES AND PROCESS FOR PRODUCING THE SAME

[75] Inventors: Tadashi Arai, 50-6, 6-chome, Nagata, Nakano-Ku, Tokyo; Yuzuru Mikami, Chiba, both of Japan

[73] Assignee: Tadashi Arai, Tokyo, Japan

[21] Appl. No.: 99,878

[22] Filed: Sep. 22, 1987

Related U.S. Application Data

[63] Continuation of Ser. No. 769,930, Aug. 27, 1985, abandoned.

[30] Foreign Application Priority Data

Aug. 30, 1984 [JP] Japan ................................. 59-179292

[51] Int. Cl.$^4$ ......................... C12P 17/18; C12P 1/04; C12R 1/56
[52] U.S. Cl. .................................. 435/119; 435/170; 435/899
[58] Field of Search .................. 435/119, 169, 170, 68, 435/70

[56] References Cited

U.S. PATENT DOCUMENTS 4,248,863  2/1981  Arai ..................................... 435/169
4,372,947  2/1983  Arai et al. ............................ 435/169

OTHER PUBLICATIONS

PCT WO85/01049, Mar. 14, 1985.
Antimicrobial Agents and Chemotherapy 28, pp. 5-11, (1985).
J. Antibiotics 37, 847-852 (1984).
Japanese 60 084288, Derwent (Abst. 85-150655/25).
Tetrahedron Letter, 25, pp. 2355-2358 (1979).

Primary Examiner—Thomas G. Wiseman
Assistant Examiner—Charles L. Patterson, Jr.
Attorney, Agent, or Firm—Wenderoth, Lind & Ponack

[57] ABSTRACT

Disclosed are compounds of the formula

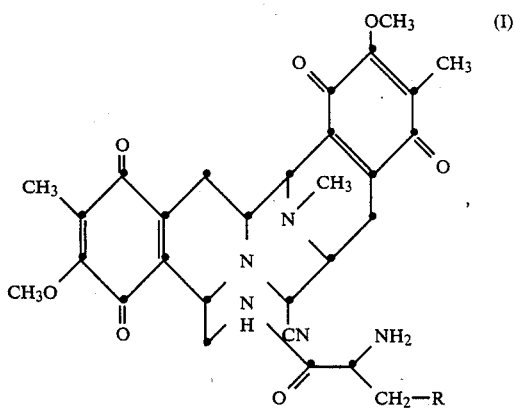

wherein R represents hydrogen or $C_1$-$C_4$-alkyl. These compounds are obtained by fermentation of the known saframycin A producing strain Streptomyces lavendulae No. 314 and by reaction with the amino acids L-tyrosine, L-methionine, glycine and HOOC-(CH)NH$_2$-CH$_2$-R. When R is hydrogen, saframycin Y$_3$ and when R is methyl, saframycin Y$_{d-1}$ are produced.

15 Claims, 4 Drawing Sheets

FIG. 1

NOVEL SAFRAMYCIN A DERIVATIVES AND PROCESS FOR PRODUCING THE SAME

This is a continuation of application Ser. No. 769,930 filed on Aug. 27, 1985, now abandoned.

The present invention relates to novel antibiotics produced by fermentation, to processes for their production, to pharmaceutical compositions containing these antibiotics and to methods of use of these antibiotics.

In the U.S. Pat. No. 4,248,863 antibiotics named saframycin A, B, C, D, and E are disclosed having antibacterial activity and activity against transplantable tumors. These antibiotics are produced by the strain Streptomyces lavendulae No. 314 which has been isolated from a soil sample collected at Kyoto, Japan and deposited on Sept. 2, 1975 in the Fermentation Research Institute, Agency of Industrial Science and Technology, Japan under the accession number FERM-P-3218.

According to T. Arai et al., Tetrahedron Letters, 25, 2355-2358 (1979) and Experientia, 36, 1024-1026 (1980) the structural formulae of these saframycin derivatives have been determined. The most active derivative of the saframycin group, saframycin A, has the structural formula:

Object of the present invention are novel saframycin A derivatives having improved pharmacological activity, especially antitumor activity, as compared to saframycin A itself.

The present invention relates to saframycin A derivatives of the general formula wherein R represents hydrogen or $C_1$-$C_4$-alkyl or an acid addition salt thereof.

In the context of the description of the present invention, the general terms employed hereinbefore and hereinafter preferably have the following meanings:

R defined as $C_1$-$C_4$-alkyl is preferably methyl, but also ethyl, isopropyl, n-propyl, isobutyl, tert-butyl or n-butyl.

R is preferably hydrogen or methyl.

Acid addition salts are preferably pharmaceutically acceptable acid addition salts with non-toxic and physiologically well tolerated acids such as diluted aqueous mineral acids, such as hydrochloric, sulfuric, or phosphoric acid, or organic acids such as lower alkane-carboxylic acid, for example acetic acid, unsaturated carbonic acids, for example fumaric or maleic acid, hydroxy-carbonic acids, for example lactic, tartic or citric acid, or aromatic acids, for example salicylic acid.

The invention especially relates to saframycin A derivatives of the formula I wherein R is hydrogen or methyl. In the description of the present invention, the saframycin A derivative wherein R is hydrogen, is named saframycin $Y_3$ and the saframycin A derivative wherein R is methyl, is named saframycin $Y_{d-1}$.

TABLE 1

Figure 1:
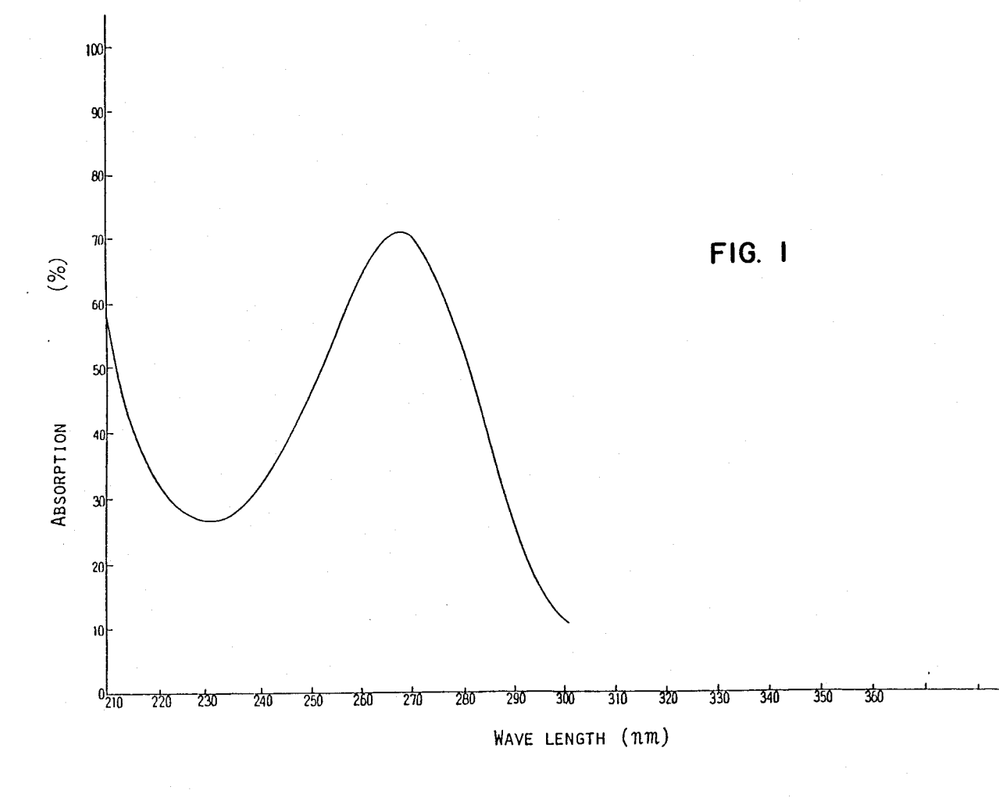
FIGS. 1 and 2 are ultraviolet (UV) and infrared (IR) absorption spectra of saframycin $Y_3$ in methanol and chloroform, respectively obtained according to the present invention.
Figure 2:
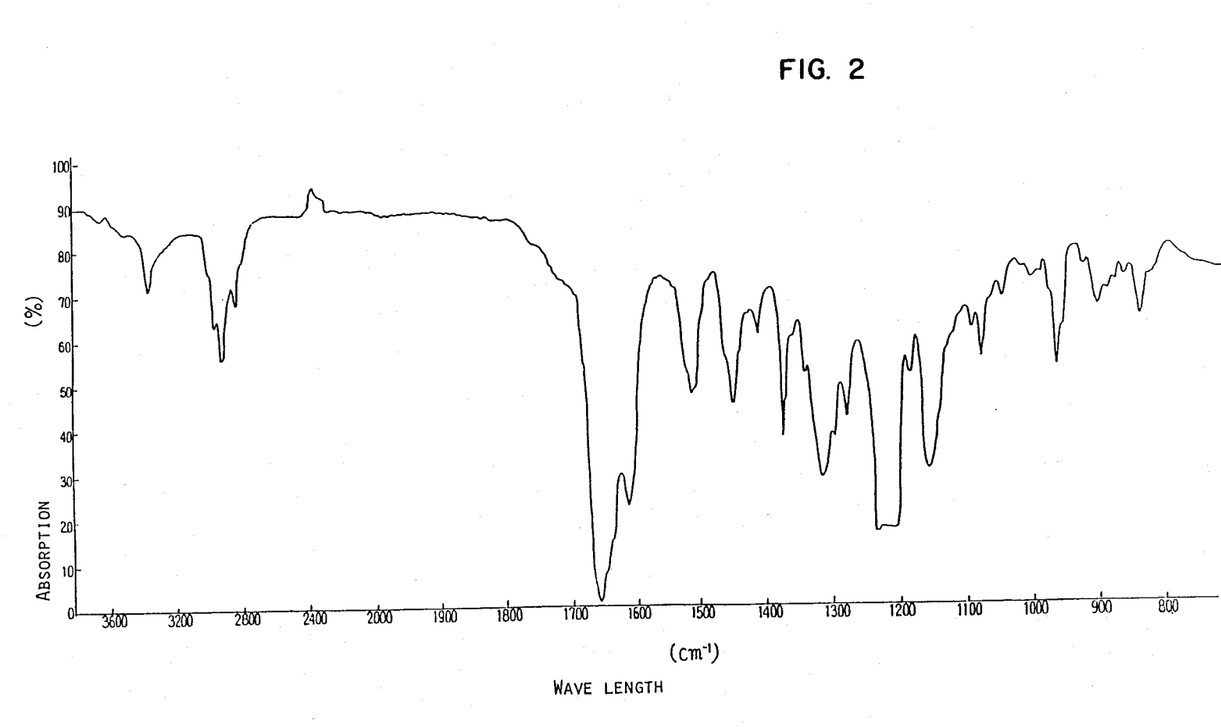
Figure 3:
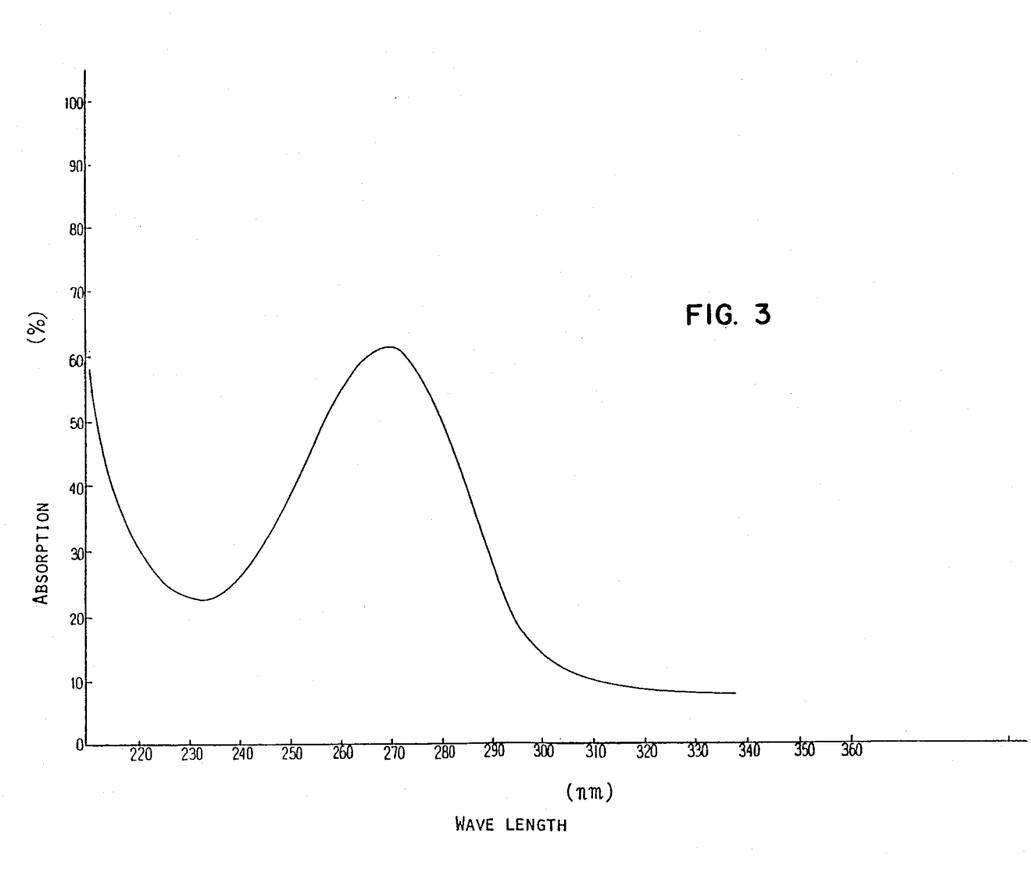
FIGS. 3 and 4 are ultraviolet and infrared absorption spectra of saframycin $Y_{d-1}$ in methanol and chloroform, respectively obtained according to the present invention.
Figure 4:
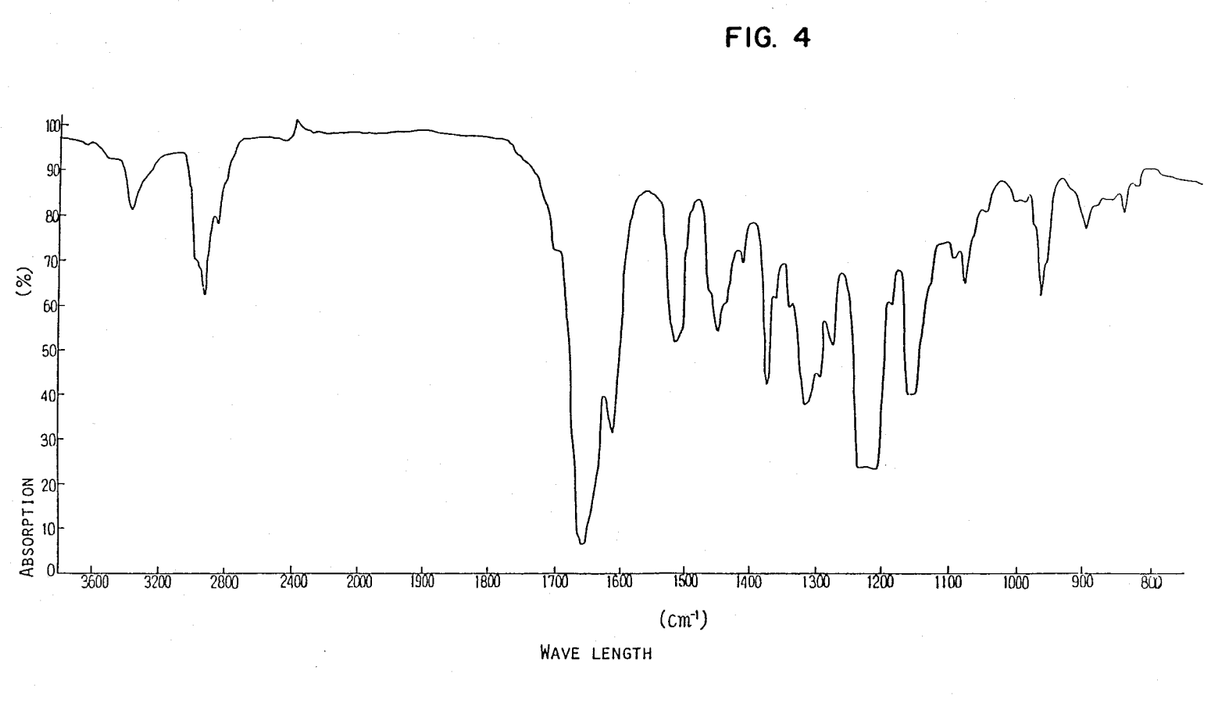

| Analytical Data of Saframycin $Y_3$ and $Y_{d-1}$ | | |
|---|---|---|
| Parameters | Saframycin $Y_3$ | Saframycin $Y_{d-1}$ |
| Color and shape | yellow powder | yellow powder |
| Melting point | 143-146° C. | 124-127° C. |
| Elementary analysis | 61.45% C | 60.78% C |
| (theoretical values | (61.81%) | (62.39%) |
| in brackets) | 5.99% H | 5.83% H |
| | (5.91%) | (6.06%) |
| | 11.91% N | 11.78% N |
| | (12.43%) | (12.13%) |
| Specific | -46.1° | -43.5° |
| Rotation $[\alpha]_D^{22}$ | (c = 0.07% methanol) | (= 1.0% methanol) |
| Ultraviolet adsorption spectrum (UV) (FIGS. 1 and 3) | | |
| $\lambda_{max}^{methanol}$ [nm (log $\epsilon$)] | 268 (4.27) 340 (sh) | 269 (4.26) |
| $\lambda_{min}^{methanol}$ [nm (log $\epsilon$)] | 232 (3.77) | 233 (3.77) |
| Infrared absorption spectrum (IR) (FIGS. 2 and 4) | | |
| $\nu_{max}^{chloroform}$ [cm$^{-1}$] | 3380, 1655 1615, 1515 | 3380, 1660, 1615, 1515 |
| Nuclear magnetic resonance spectrum (NMR) (CDCl$_3$) [$\delta$ (ppm)] | 7.23* (1 H, d-d) | 7.25* (1 H. d-d) |
| | 4.07 (1 H, bs) | 4.05 (3 H, S) |
| | 4.06 (3 H, s) | 4.03 (3 H, s) |
| | 4.03 (3 H, s) | 4.01 (1 H, d) |
| | 4.00 (1 H, d) | 3.91 (1 H, bs) |
| | 3.94 (1 H, bs) | |
| | 3.83 (1 H, d-d-d) | 3.83 (1 H, d-d-d) |
| | 3.45 (1 H, d-d) | 3.45 (1 H, d-d) |
| | 3.27 (1 H, q) | 3.14 (1 H, t-d) |
| | 3.15 (1 H, t-d) | 3.06 (1 H, t-d) |
| | 3.00 (1 H, t-d) | 3.05 (1 H, t) |
| | 2.88 (1 H, d-d) | 2.86 (1 H, d-d) |
| | 2.82 (1 H, d-d) | 2.32 (1 H, d) |
| | 2.33 (3 H, s) | 2.32 (3 H, s) |
| | 2.27 (1 H, d) | 1.93 (3 H, s) |
| | 1.92 (3 H, s) | 1.89 (3 H, s) |
| | 1.88 (3 H, s) | 1.48 (1 H, m) |
| | 1.62 (2 H, b) | 1.45* (2 H, b) |
| | 1.37 (1 H, d-d-d) | 1.35 (1 H, d-d-d) |
| | 0.92 (3 H, d) | 1.06 (1 H, m) |
| | | 0.74 (3 H, t) |
| Solubility | | |
| soluble in: | lower alcohols, chloroform, esters, acetone, and benzene | |
| slightly soluble in | ethyl ether | |
| insoluble: | water. n-hexane | |

TABLE 1-continued

Analytical Data of Saframycin $Y_3$ and $Y_{d-1}$

| Parameters | Saframycin $Y_3$ | Saframycin $Y_{d-1}$ |
|---|---|---|
| Color reactions | | |
| Dragendorff | positive | |
| ninhydrin | positive | |
| ironperchlorate | negative | |
| anthrone | negative | |

*interchangeable with $D_2O$

Saframycin A derviatives of the formula I, especially saframycins $Y_3$ and $Y_{d-1}$, as well as their acid addition salts, have valuable pharmacological properties. In particular, they have antimicrobial and antitumor activities and can, therefore, be used therapeutically in the form of pharmaceutical preparations for the treatment of infections of humans and animals caused by bacteria and fungi and/or, preferably, for the treatment of tumors.

With respect to the antimicrobial activities of saframycins $Y_3$ and $Y_{d-1}$, the antibacterial spectra in vitro, as expressed by their minimum inhibitory concentrations (MIC), are shown in Table 2:

TABLE 2

Antibacterial Spectra of Saframycins $Y_3$ and $Y_{d-1}$

| | | | MIC [mcg/ml] | |
|---|---|---|---|---|
| Strain | IFM No. | Medium | Saframycin $Y_3$ | $Y_{d}$* |
| Staphylococcus aureus 209 P | 2014 | A | 1 | 1 |
| Staphylococcus aureus Smith | 2018 | A | 0.1 | 1 |
| Staphylococcus albus | 2013 | A | 1 | 10 |
| Staphylococcus citreus | 2025 | A | 0.1 | 0.1 |
| Sarcina lutea | 2066 | A | 1 | 1 |
| Bacillus subtilis PCI 219 | 2060 | A | 10 | 1 |
| Bacillus cereus | 2058 | A | 50 | 50 |
| Escherichia coli F1 | 3002 | A | 50 | 50 |
| Salmonella typhimurium | 3023 | A | 50 | 50 |
| Shigella dysenteria | 3024 | A | 10 | 10 |
| Klebsiella pneumoniae | 3008 | A | 10 | 10 |
| Serratia marcescens | 3029 | A | 50 | 50 |
| Pseudomonas aeruginosa | 3011 | A | >100 | >100 |
| Streptococcus faecalis | 2001 | B | 10 | 10 |
| Streptococcus pyogenes Cook | 2003 | B | <0.001 | <0.001 |
| Streptococcus pyogenes 090 R | 2006 | B | 0.1 | 0.01 |
| Streptococcus salivarius | 2010 | B | 50 | 50 |
| Corynebacterium diphtheria | 2056 | B | <0.001 | <0.001 |
| Corynebacterium xeriosis | 2057 | B | 1 | 1 |
| Mycobacterium sp. 607 | 2051 | B | >100 | >100 |
| Mycobacterium phlei | 2052 | B | 50 | 50 |
| Mycobacterium avium 2054 | B | 50 | 50 | |
| Nocardia asteroides | 0006 | B | 50 | 1 |
| Brucella abortus | 3032 | B | 1 | 1 |
| Candida albicans 7N | 40009 | C | >100 | >100 |
| Saccharomyces cerevisiae | 40025 | C | >100 | >100 |
| Rhodotorula glutinus | 40057 | C | >100 | >100 |
| Aspergillus niger | 40606 | C | >100 | >100 |
| Aspergillus oryzae | 40601 | C | >100 | >100 |
| Penicillium expansum | 40618 | C | >100 | >100 |
| Trichophyton mentagrophytes | 40134 | C | >100 | >100 |

Medium: A=nutrient agar, B=glucose (0.5%) agar, C=Sabouraud's glucose (2%) agar.

All MIC-values shown in Table 2 are obtained from cultures on agar plates containing varying amounts of the antibiotic tested at temperatures of 37° C. after an incubation period of 24 hours (bacteria), 48 hours (fungi except *candida albicans*, 37° C., 48 hours, *Trichophyton mentagrophytes*.

The antitumor activities of saframycin $Y_3$ and $Y_{d-1}$ have been determined as follows:

In cell cultures of mouse leukaemia L 1210, the $ED_{50}$ (cytotoxic effect) of saframycin $Y_3$ is 0.0016 mcg/ml and of saframycin $Y_{d-1}$ 0.002 mcg/ml.

In another test, ICR mice (10 mice per group) were inoculated with Ehrlich ascitic tumor cells. Twenty-four hours after the inoculation the dose of 20 micrograms/mouse/day of saframycin $Y_3$ or 20 micrograms/mouse/day of saframycin $Y_{d-1}$ was administered intraperitoneally. The administration was continued for 7 days. As the result, all mice survived. When 5 micrograms/mouse/day of saframycin $Y_3$ or 4 micrograms/mouse/day of $Y_{d-1}$ were administered, 60–70% of the mice survived for 20 days or more.

In another test, the effect of saframycins $Y_3$ and $Y_{d-1}$ against mouse leukemia L 1210 was examined by using $BDF_1$ mice according to the procedure as established by the US National Cancer Research Institute. When administered intraperitoneally for a period of one week from 24 hours after the transplanation of the tumor, saframycin $Y_3$ exhibited a survival effect [T (days, number of surviving mice in the administered group)/C (days, number of surviving mice in the control group)×100] of 130% at a dose of 10 micrograms/mouse/day and saframycin $Y_{d-1}$ exhibited a survival effect [T/C×100] of 140% at the same dose as above, both demonstrating a prolongation in the period of survival. Both of these values exceed the critical level of effectiveness prescribed by the above-mentioned research institute.

In another test, the effect of saframycin $Y_{d-1}$ against metastasis of Lewis lung cancer was determined in the following manner:

The foot pads of the left hind legs of $BDF_1$ mice having a body weight of 20 g were subcutaneously inoculated with $1.5 \times 10^5$ Lewis lung cancer cells. After seven days the legs were amputated.

A physiological sodium chloride solution was administered intraperitoneally to the control group while saframycin $Y_{d-1}$ was given at a dose of 40 micrograms/mouse/day for 10 days i.p. to the group to be treated. Seven days after the last administration, the mice were sacrificed and the spread of metastasis in the lungs was compared. In the control group, abundant metastasis in the lungs was found while in the treated group metastasis was scarcely observed. In anther experiment, the effect against Lewis lung cancer was evaluated according to the guidelines of the USA Cancer Institute (R. L. Geran et al. Cancer Chemotherapy Reports, Part 3, Vol. 3, No. 2 (1972)). Thus, when saframycin $Y_{d-1}$ was administered intraperitoneally at a dose of 20 micrograms/mouse/day for 10 days, [T/C×100] was 140% or higher, thus demonstrating that saframycin had a higher preventing effect against cancer metastasis as compared to saframycin A.

The present invention also relates to pharmaceutical preparations which contain as active ingredient a compound of the formula I, or a pharmaceutically acceptable acid addition salt thereof, as well as to processes for the production of these pharmaceutical preparations. The pharmaceutical preparations of the present invention are useful for oral or parenteral administration and they contain exclusively the pure pharmacologically active compound (I) itself or this compound in combination with suitable pharmaceutically acceptable carriers.

The pharmacologically active compounds of the present invention are preferably used in the form of parenterally, for example i.v. or i.p. administrable preparations or in the form of infusion solutions. Such preparations or solutions are preferably isotonic aqueous solutions or suspensions, such as oily injection suspensions. These solutions or suspensions can be prepared before use, for example from lyophilised preparations that contain the pure active compound itself or in combination with a carrier, for example mannitol. The pharmaceutical preparations are sterilized and/or may contain adjuncts, for example preservatives, stabilisers, wetting agents and/or emulsifying agents, solubilisers, salts for regulating the osmotic pressure and/or buffers. Aqueous injection suspensions can be prepared by admixture with substances that increase the viscosity, for example sodium carboxymethylcellulose, sorbitol and-/or dextran, and optionally stabilisers. The present pharmaceutical preparations which, if desired, may contain further pharmacologically valuable compounds, are manufactured in a manner known per se, for example by means of conventional dissolution or lyophilisation processes, and contain from approximately 0.1% to 100%, especially from approximately 1% to approximately 50%, in the case of lyophilisates up to 100%, of the active compound.

Suitable for enteral, for example oral, administration to humans or warm-blooded animals are pharmaceutical preparations that contain from approximately 10% to approximately 90%, especially from 20 to 75%, of the pure active compound itself in combination with a pharmaceutically acceptable carrier. These preparations are prepared in the form of dosage units, such as dragées, tablets, capsules, suppositories or ampoules. They are manufactured in a manner known per se, for example by means of conventional mixing, granulating, coating, dissolution or lyophilisation processes.

Suitable carriers for the preparation of tablets and/or dragées are especially filling materials, such as sugars, for example lactose, saccharose, mannitol or sorbitol, cellulose preparations and/or calcium phosphates, for example tricalcium phosphate or calcium biphosphate, also binders, such as starch pastes with the use of, for example maize, wheat, rice or potatoe starch, gelatin, tragacanth, methylcellulose, hydroxypropylmethylcellulose, sodium carboxymethylcellulose and/or polyvinylpyrrolidone, and/or, if desired, disintegrating agents, such as the above-mentioned starches, also carboxymethyl starch, cross-linked polyvinylpyrrolidone, agar, alginic acid or a salt thereof, such as sodium alginate. Adjuncts are expecially flow regulators and lubricants, for example silica, talcum, stearic acid or salts thereof, such as magnesium or calcium stearate, and/or polyethylene glycol. Dragée cores are provided with suitable coatings that are optionally resistant to gastric juices. Inter alia, concentrated sugar solutions are being used which optionally contain gum arabic, talcum, polyvinylpyrrolidone, polyethylene glycol and/or titanium dioxide, lacquer solutions in suitable organic solvents or solvent mixtures, or, for the manufacture of coatings that are resistant to gastric juices, solutions of suitable cellulose preparations, such as acetylcellulose phthalate or hydroxypropylmethylcellulose phthalate. Dyes or pigments may be added to the tablets or dragée coatings, for example for identification or indication of different quantities of the active compounds.

Further pharmaceutical preparations for oral use are dry-filled capsules of gelatin, and soft closed capsules of gelatin and a plasticiser, such as glycerine or sorbitol.

The invention also relates to methods of use of the new compounds (I) and their pharmaceutically acceptable acid addition salts as pharmacologically active compounds, preferably in the form of pharmaceutical preparations. The dosage of the active compound depends on the species, body weight, age and individual condition, and also on the mode of administration. On average a daily dose within the range from 3 mg to 40 mg, of the active compound is administered to a human or warm-blooded animal of approximately 70 kg body weight.

The new compounds can also be used in veterinary medicine.

The present invention also relates to a process for preparing by fermentation saframycin A derviatives of the formula I wherein R represents hydrogen or $C_1$–$C_4$-alkyl, and acid addition salts thereof, characterized in that (a) a preculture is prepared by inoculation of a culture medium containing a carbon and a nitrogen source and essential trace elements with a strain of the genus streptomyces which is capable of producing saframycin A, and culturing at a temperature of approximately 25°–35° C. and a pH level of approximately 4.0–7.5 under aerobic conditions, the biomass obtained is isolated, an aqueous suspension of this biomass is reacted with an amino acid of the formula HOOC—CH(NH$_2$)—CH$_2$—R, wherein R denotes hydrogen or $C_1$–$C_4$-alkyl, and with glycine, L-tyrosine and L-methionine or a peptide formed by any of the amino acids selected from the group consisting of HOOC—CH(NH$_2$)—CH$_2$—R, glycine, L-tyrosine, or L-methionine, a cyanide salt is added to the culture filtrate, and the saframycin A derivative of the formula I obtained is isolated and purified and, optionally, converted to an acid addition salt, or (b) for the preparation of the saframycin A derivative of the formula I wherein R represents hydrogen (saframycin Y$_3$)-a culture is prepared by inoculating a culture medium containing a carbon and nitrogen source and essential trace elements with a strain of the genus streptomyces which is capable of producing saframycin A, and culturing at a temperature from approximately 25°–35° C. and at a pH level from approximately 4.0 to 7.5 under aerobic conditions, and saframycin Y$_3$ obtained is isolated and purified and, optionally, converted to an acid addition salt.

Process (a)

Carbon sources: Carbohydrates such as D-glucose, maltose, D-fructose, L-arabinose, or sucrose or salts of organic acids such as sodium acetate, sodium citrate or sodium succinate.

Nitrogen sources: Meat extracts, Polypeptone ® (Wako Chemical Industries) polypeptone, tryptone, gluten, cottonseed oil, soybean flour, corn starch liquor, dried yeast, yeast extract, urea, ammonium salts, for example ammonium chloride or sulfate, or nitrates, for example potassium or ammonium nitrate.

Essential trace elements are added to the preculture in the form of inorganic salts. Such salts are, for example, water-soluble halides, for example chlorides, carbonates, sulphates or phosphates of alkali metals, for example sodium or potassium, alkaline earth metals, for example calcium or magnesium, or transition metals, for example iron, manganese, molybdenum, copper or zinc.

In case nitrogen sources from meat or plants are used, such as meat extracts, protein digests or peptone etc., the addition of essential trace elements is facultative, as these elements may be present in the nitrogen sources mentioned.

A strain of the genus streptomyces capable of producing saframycin A is, preferably, the strain Streptomyces lavendulae No. 314 mentioned above or a mutant derived from this microorganism which is also capable of producing saframycin A.

The isolation and purification of Streptomyces lavendulae No. 314 from a soil sample of the Kyoto area as well as the taxonomic classification of this strain has been disclosed in the U.S. Pat. No. 4,248,863 and is incorporated here by reference.

From the strain Streptomyces lavendulae No. 314 mutants can form spontaneously (natural mutants) or artificial mutants can be produced which, like the natural strains, are capable of producing saframycin A in aqueous solution and produce biomass. Such mutants can be produced by chemical means, for example by treatment with certain guanidine derivatives, for example N-methyl-N'-nitro-N-nitrosoguanidine or with an alkali nitrite, for example sodium nitrite, or by physical means, for example by exposure to ultraviolet, X-ray or radioactive radiation.

Culturing is effected under aerobic conditions, for example in an atmosphere containing oxygen, oxygen enriched air or air, and while shaking or stirring in shaking flasks or fermenters. Submerged cultures by permanent stirring are preferred. Culturing can be carried out within a temperature range from approximately 25° to approximately 35° C., preferably from approximately 27° to approximately 30° C.

Culturing can be carried out batchwise, for example by single or repeated addition of nutrient solution, or continuously by continuous addition of nutrient solution.

Culturing is preferably effected in several stages, first by preparing one or more cultures prior to the preculture mentioned above. The first culture is prepared in a synthetic nutrient medium, preferably Krainsky agar slant culture, [Natur. Centr. Bakteriol. Parasitenk., Abt. II, 41, 649–688 (1914)] containing bacto-agar (Difco), glucose, asparagine, $KH_2PO_4$ and distilled water. This culture is transferred to another culture containing the carbon and nitrogen sources as well as the essential trace elements mentioned above. This culture is then transferred to the actual main preculture mentioned above. When preparing the precultures, the same fermentation conditions are maintained.

The course of the fermentation can be monitored analytically by taking samples, for example by measuring the optical density which is a measure of the growth of the particular strain, as well as by gravimetric analysis on the basis of the dry weight of the biomass formed.

In case foams are produced during the fermentation, an antifoaming agent such as silicone, vegetable oil (soybean oil) or mineral oil antifoaming agent such as polyoxyalkylene, Adecanol ®️ and the like are added.

Biomass or mycel is formed, for example, by fermentation of the microorganisms mentioned above and is cell material present in the living state, for example in the state of replication or resting, or is cell material in the state of partial or complete cell death, or is already in the state of enzymatic decomposition or decomposition by other cultures. Such biomass can be separated from the aqueous phase by conventional separation methods, for example filtration, centrifugation or sedimentation.

The biomass or mycel collected from the culture medium is subsequently resuspended in an aqueous phase capable of maintaining the living activity of the microorganisms, preferably in an aqueous isotonic sodium chloride solution or in 0.1M MES (2-(n-morpholino)-ethane-sulfonic acid monohydrate) buffer.

Preferably, about 5 g of biomass are suspended in 100 ml water. To this suspension the amino acids L-methionine, L-tyrosine, glycine and $HOOC—CH(NH_2)—CH_2—R$ wherein R denotes hdyrogen or $C_1$-$C_4$-alkyl, or a peptide formed by any of the amino acids selected from the group consisting of $HOOC—CH(NH_2)—CH_2—R$, glycine, L-tyrosine, or L-methionine, preferably the dipeptide formed by glycine and the amino acid $HOOC—CH(NH_2)—CH_2—R$, are added and the reaction mixture is subjected to aeration, shaking or agitation as mentioned above.

If L-tyrosine, L-methionine, glycine and L-alanine are added, saframycin $Y_3(R=H)$ is produced. Instead of L-alanine, an excess of D,L-alanine can also be added. Only the L-isomer is used for producing saframycin $Y_3$. Glycine and L-alanine can also be added as L-alanylglycine dipeptide. If L-tyrosine, L-methionine, glycine, and 2-amino-n-butyric acid are added, saframycin $Y_{d-1}$ ($R=CH_3$) is produced. Glycine and 2-amino-n-butyric acid can be added as 2-amino-n-butyrylglycine dipeptide.

The biomass is removed from the aqueous phase by conventional separation techniques, e.g. filtration, after reaction with the amino acids and peptides mentioned above. To the culture filtrate an exess amount of a cyanide salt, e.g. an alkalimetal cyanide salt, for example sodium or potassium cyanide, is added.

The products according to the present invention are extracted from the culture filtrate under weakly alkaline conditions with an organic solvent immiscible with water, for example methylene chloride. The solvent is removed, for example by destillation under reduced pressure. The residue obtained is dissolved in an organic solvent, e.g. ethyl acetate, and the organic solution is acidified, for example by adding a solution of aqueous acetic acid. The acidic aqueous layer containing the product is made weakly alkaline, for example by adding aqueous ammonia or an aqueous sodium carbonate solution. The product is again extracted by an organic solvent, e.g. ethyl acetate. Depending on the degree of purity desired the extraction processes are repeated. The solvent is distilled off from the organic solution, the residue is dried and the crude product obtained is purified by silica column chromatography.

Process (b)

The preparation of the culture may be carried out in the same manner as the preparation of the preculture described in process (a). The same carbon sources (D-glucose, maltose, fructose, etc.) and nitrogen (meat extracts, protein digests such as peptone etc.) are used and the same fermentation conditions (aeration of the submerged cultures, temperature 25°–35° C., preferably 27°–30°). Analogous to process (a), one or more precultures prior to the main culture may be subsequently prepared.

After fermentation, the culture broth is separated by conventional separation techniques, e.g. filtration, and the culture filtrate is subjected to extraction processes. Mainly saframycin A is obtained and saframycin $Y_3$ is isolated as byproduct. Before extraction, the filtrate is adjusted to pH 8.0 by addition of 10N aqueous sodium hydroxide solution. If desired, the filtrate may previously be concentrated to ½ or ⅓ its original volume in order to enhance the efficiency of extraction with organic solvent such as chloroform or dichlormethane.

Upon this solvent extraction, the basic and water-soluble antibiotic streptothricin simultaneously formed by the streptomyces strain mentioned above remains in the filtrate, while saframycin derivatives are extracted into the organic solvent layer. The solvent layer is evaporated to dryness under reduced pressure, and the residue is dissolved in a small amount of an organic solvent, e.g. ethyl acetate. The resulting solution is then shaken with an aqueous solution of sodium carbonate and separated into phases, whereby acidic compounds are transferred into the aqueous phase. Then, the organic phase is extracted with an acid, e.g. 1N hydrochloric acid, all aqueous extract layers are again made alkaline to pH 8-9 with aqueous ammonia, and are extracted again with organic solvent, e.g. chloroform. After repeating these procedures several times, the solvent layer is concentrated to dryness under reduced pressure, whereby a crude product is obtained containing various saframycin derivatives. The crude product is purified on a chromatographic column of silica gel and eluted with a mixture of benzene and ethyl acetate. A fraction consisting mainly of saframycin A is obtained. This fraction is divided into fractions of saframycin A and $Y_3$ by passing through another chromatographic column of silica gel and elution with methyl alcohol. These fractions are further purified by gel filtration, for example with a Sephade LH-20 ® column.

The following Examples illustrate the invention without limiting the scope thereof. Temperatures are given in degrees Celsius.

EXAMPLE 1

(a) A culture medium containing 0.1% glucose, 1.0% starch, 1.0% Polypeptone, 0.5% meat extract, 0.3% NaCl and 0.01% Silicone KM 72F (Shintsu Kagaku Co. Japan) is separately poured into 12 shaking flasks (100 ml per flask) and is sterilized under elevated pressure at 120° for 15 minutes. A sample of the Streptomyces Lavendulae No. 314 strain (FERM-P 3218) is subjected to Klainsky agar slant culture for 2 weeks, from which the spores are collected. The spores are inoculated into the flasks in a quantity of two platinum loopful of spores per flask. The flasks are shaken at 27° for 30 hours. One liter of this culture medium is inoculated into a 200 l fermenter containing 100 l of a culture medium (pH 7.0) comprising 0.5% glucose, 0.5% starch, 1.0% Polypeptone, 0.5% meat extract, 0.3% NaCl and 0.02% Adecanol LG-109 (Asahi Denka Co. Japan) and is agitated at 27° for 15 hours at an aeration speed of 100 l/min. The culture fluid is filtered with a filter press, the cells are collected and washed with 60 l of isotonic sodium chloride solution. The washed cells are suspended in 30 l of isotonic sodium chloride solution and are poured into a fermenter having a capacity of 40 l.

(b) To this cell suspension 14 g glycine, 32 g DL-alanine, 24 g L-methionine and 12.5 g tyrosine are added. The cell suspension is adjusted to pH 5.9 with 0.5N sulfuric acid and incubated under stirring at 27° at an aeration speed of 20 l/min. After reacting for six hours, the culture fluid is filtered, 2.5 g of sodium cyanide is added to the filtrate and the resulting mixture is stirred for another hour. The filtrate is extracted with 15 l of dichloromethane.

(c) The dichloromethane extract layer is concentrated under reduced pressure. The crude extract thus obtained is a dark brown-colored oily substance and is dissolved in about 300 ml of ethyl acetate. This solution is extracted with two 150 ml portions of 10% aqueous acetic acid. The aqueous acetic acid layers are combined, and their pH is adjusted to 8-9 by adding concentrated aqueous ammonia or sodium carbonate solution while cooling with ice. The aqueous layer is extracted with two 200 ml portions of ethyl acetate. The organic solvent layer is repeatedly washed neutral with water. After drying over anhydrous sodium sulfate, the solvent is distilled off under reduced pressure. Saframycin $Y_3$ is obtained as a yellow powder. This crude powder is dissolved in a small amount of ethyl acetate and subjected to silica gel chromatography. About 85 g of silica gel (manufactured by Merck, 70-230 mesh) are suspended in a 1:1 mixture of ethyl acetate and benzene and packed in a glass column having an inner diameter of 1.5 cm. The solution containing the product is percolated through the column and is eluted with about 200 ml of a 1:1 mixture of ethyl acetate and benzene, and with 200 ml portions of ethyl acetate, ethyl acetate containing 1% methanol, ethyl acetate containing 5% methanol and ethyl acetate containing 10% methanol, successively. Most of saframycin $Y_3$ is eluted by eluents consisting of ethyl acetate and ethyl acetate containing 1% methanol. A minor portion is eluted into the ethyl acetate eluent containing 2-5% of methanol. The crude saframycin $Y_3$ obtained is purified by silica gel thin layer chromatography (E. Merck, 60 F 254). After developing with a solvent system consisting of chloroform and ethanol (10:1), a yellow band having an Rf value of approximately 0.3 is extracted with ethyl acetate containing 10% of methanol. The solvent is removed under reduced pressure. The product is dissolved in a small amount of ethyl acetate or benzene, and ether is added to the solution under cooling with ice. Pure saframycin $Y_3$ is obtained as a yellow powder. M.p. 143°-146°.

EXAMPLE 2

(a) Two fermenters are charged with 6 l portions of GSB (glucose-starch-bouillon) medium containing 0.5% glucose, 0.5% starch, 1% Polypeptone, 0.5% meat extract, 0.3% NaCl and 0.02% Adecanol LG-109 (pH 7.0). Streptomyces lavendulae No. 314 strain is pre-cultured in the same medium as above at 27° for 18 hours in an Erlenmeyer flask. The culture product is inoculated into the fermenters in a concentration of 10%, and is fermented at 27° at an aeration speed of 10 l/min. 15 hours after the start of culturing and one hour after the cells are colored blue, the cells are collected by centrifugation. The collected cells are washed twice with 0,01M MES buffer (pH 5.75) and are suspended in 12 l of 0.01M MES buffer.

(b) 20 g 2-amino-n-butyrylglycine, 16 g L-methionine and 8 g tyrosine are added to the cell-suspension which is separately poured into 500 ml Erlenmeyer flasks (100 ml of suspension per flask) and incubated at 27° C. for 6 hours at a stirring speed of 300 r.p.m. (rotations per minute). Then the reaction mixtures are combined and filtered to remove the cells. After adding 1 g of sodium cyanide, the filtrate is allowed to react for an additional hour and is then extracted with 5 l of dichloromethane.

(c) The dichloromethane extract is concentrated under reduced pressure. The crude extract obtained is a dark brown oily substance which is dissolved in about 100 ml ethyl acetate. The resulting solution is extracted with two 50 ml portions of 10% aqueous acetic acid. The aqueous layers are combined and their pH is adjusted to 8-9 by adding concentrated aqueous ammonia or sodium carbonate solution while cooling with ice.

The aqueous layer is extracted with two 100 ml portions of ethyl acetate. The organic layer is repeatedly washed neutral with water. After drying over anhydrous sodium sulfate, the solvent is distilled off under reduced pressure. Saframycin $Y_{d-1}$ is obtained as yellow powder. The crude powder is dissolved in a small amount of ethyl acetate and subjected to silica gel chromatography. About 50 g of a silica gel (Merck, 70-230 mesh) are suspended in a 1:1 mixture of ethyl acetate and benzene and are packed in a glass column having an inner diameter of 1.0 cm. The solution containing the product is percolated through the column and is eluted with about 150 ml of a 2:1 mixture of ethyl acetate and benzene, subsequently with 150 ml of ethyl acetate, and then with 100 ml portions of ethyl acetate containing 5% methanol and ethyl acetate containing 10% methanol, successively. Most of Saframycin $Y_{d-1}$ is eluted by the ethyl acetate fraction. The crude Safamycin $Y_{d-1}$ thus obtained is purified by silicagel thin layer chromatography (E. Merck, 60 F 254). Thus, after developing with a solvent system consisting of chloroform and ethanol (10:1), a yellow band having an Rf value of about 0.4 is extracted with ethyl acetate containing 10% methanol. This procedure is repeated twice. The solvent is removed under reduced pressure and the product is dissolved in a small amount of ethyl acetate or benzene. After the addition of ether under cooling with ice, saframycin $Y_{d-1}$ is obtained as yellow powder. M.p. 124°-127°.

EXAMPLE 3

In a manner analogous to Example (1a), a culture medium containing Streptomyces lavendulae No. 314 is prepared. After filtration with a filter press, the filtrate is extracted with dichloromethane. The dichloromethane phase is treated in a manner analogous to Example (1c) and saframycin $Y_3$ is obtained as a yellow powder.

What is claimed is:

1. A process for the preparation of a compound of the formula (I)

wherein R represents hydrogen or $C_1$-$C_4$-alkyl comprising
    (a) suspending a biomass of a strain of streptomyces capable of producing saframycin A in an aqueous medium;
    (b) adding to said suspension glycine, L-tyrosine, L-methionine, and an amino acid of the formula $$HO_2CCH(NH_2)-CH_2-R \quad (II)$$

wherein R is as defined above, either as individual amino acids or peptides consisting of amino acids selected from glycine, L-tyrosine, L-methionine, and the amino acid of formula II, or mixtures of said amino acids and said peptides to yield an enriched suspension;
    (c) incubating said enriched suspension;
    (d) filtering the result of step c; and
    (e) adding a cyanide salt to the filtrate obtained from step d to result in said compound of formula I.

2. The process of claim 1 which further comprises isolating said compound of formula I from the result of step e.

3. The process of claim 1 which further comprises converting said compound of formula I to an acid addition salt thereof.

4. The process of claim 3 wherein said acid addition salt is pharmaceutically acceptable.

5. The process of claim 1 wherein said biomass is obtained by inoculating a culture medium containing a carbon source, a nitrogen source, and essential trace elements with a strain of streptomyces capable of producing saframycin A; culturing said inoculated medium at a temperature of about 25° C. to about 35° C., at a pH of about 4.0 to about 7.5, under aerobic conditions to yield a biomass in said culture; and isolating said biomass therefrom.

6. A process for the preparation of a compound of the formula (I)

wherein R represents hydrogen comprising
    (a) suspending a biomass of a strain of streptomyces capable of producing saframycin A in an aqueous medium;
    (b) adding to said suspension glycine, L-tyrosine, and L-methionine, either as individual amino acids or as peptides consisting of glycine, L-tyrosine, and L-methionine, or mixtures of said amino acids and said peptides to yield an enriched suspension;
    (c) incubating said enriched suspension;
    (d) filtering the result of step c;

(e) adding a cyanide salt to the filtrate obtained from step d to result in said compound of formula I; and
(f) then isolating the compound of formula I.

7. The process of claim 6 which further comprises converting said compound of formula I to an acid addition salt thereof.

8. The process of claim 7 wherein said acid addition salt is pharmaceutically acceptable.

9. The process of claim 6 wherein said biomass is obtained by inoculating a culture medium containing a carbon source, a nitrogen source, and essential trace elements with a strain of streptomyces capable of producing saframycin A; culturing said inoculated medium at a temperature of about 25° C. to about 35° C., at a pH of about 4.0 to about 7.5, under aerobic conditions to yield a biomass in said culture; and isolating said biomass therefrom.

10. The process of claim 1 wherein said strain of streptomyces capable of producing saframycin A is Streptomyces lavendulae No. 314 (FERM-P 3218).

11. The process of claim 6 wherein said strain capable of producing saframycin A is Streptomyces lavendulae No. 314 (FERM-P 3218).

12. The process of claim 1 wherein R is hydrogen.

13. The process of claim 1 wherein R is methyl.

14. A process for the preparation of a compound of the formula (I)

wherein R represents hydrogen or $C_1$-$C_4$-alkyl comprising (a) suspending a biomass of a strain of streptomyces capable of producing saframycin A in an aqueous medium;
(b) adding to said suspension glycine, L-tyrosine, L-methionine, and an amino acid of the formula wherein R is as defined above, either as individual amino acids or peptides consisting of amino acids selected from glycine, L-tyrosine, L-methionine, and the amino acid of formula II, or mixtures of said amino acids and said peptides to yield an enriched suspension; and
(c) incubating said enriched suspension to result in a compound of formula I.

15. A process for the preparation of a compound of the formula (I)

wherein R represents hydrogen comprising
(a) suspending a biomass of a strain of streptomyces capable of producing saframycin A in an aqueous medium;
(b) adding to said suspension glycine, L-tyrosine, and L-methionine, either as individual amino acids or as peptides consisting of glycine, L-tyrosine, and L-methionine, or mixtures of said amino acids and said peptides to yield an enriched suspension; and
(c) incubating said enriched suspension and isolating said compound of formula I wherein R is hydrogen.

* * * * *